US00PP29757P3

(12) United States Plant Patent
van Langen

(10) Patent No.: US PP29,757 P3
(45) Date of Patent: Oct. 16, 2018

(54) ***ECHEVERIA* PLANT NAMED 'AMIECH1602'**

(50) Latin Name: ***Echeveria pulidonis* E. Walther**
Varietal Denomination: AMIECH1602

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 41 days.

(21) Appl. No.: 15/530,335

(22) Filed: Dec. 23, 2016

(65) Prior Publication Data

US 2018/0054945 P1 Feb. 22, 2018

(30) Foreign Application Priority Data

Aug. 19, 2016 (QZ) ..... PBR 2016/2027

(51) Int. Cl.
*A01H 5/00* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Echeveria pulidonis* cultivar named 'AMIECH1602' which is characterized by a flattened globular plant shape with thick succulent foliage tightly arranged in a compact rosette, broad obovate to broad oblanceolate foliage with an obtusely cuspidate apex, foliage which is upwardly curled, foliage which is moderately pruinose with a blue-grey general coloration and pink margins, as well as the stability of these characteristics from generation to generation.

4 Drawing Sheets

Latin name of the genus and species: The Latin name of the genus and species of the novel variety disclosed herein is *Echeveria pulidonis* E. Walther.

Variety denomination: The inventive variety of *Echeveria* disclosed herein has been given the variety denomination 'AMIECH1602'.

CROSS REFERENCE TO RELATED APPLICATIONS

This application claims priority to the Community Plant Variety Rights application number 2016/2027, filed Aug. 19, 2016, which is herein incorporated by reference.

BACKGROUND OF THE INVENTION

Parentage: 'AMIECH1602' is a seedling selection resulting from the self-pollination of the species, *Echeveria pulidonis* (unnamed and unpatented). The self-pollination event occurred in the summer of 2009 at a commercial greenhouse in Heerhugowaard, the Netherlands. Seed was harvested by the inventor, then germinated, and the resulting seedlings were then grown to a mature size. In spring of 2011, one seedling was observed to exhibit unique foliage characteristics and growth habit. The seedling was isolated for further evaluation in order to confirm the distinctness and stability of the characteristics first observed. Upon confirmation of distinctness and stability, 'AMIECH1602' was selected for commercialization in the summer of 2011.

Asexual Reproduction: Asexual reproduction of the new cultivar 'AMIECH1602', by way of rooting leaf cuttings, was first initiated in the spring of 2012 at the inventor's commercial greenhouse in Heerhugowaard, the Netherlands.

Through six subsequent generations, the unique features of this cultivar have proven to be stable and true to type.

SUMMARY OF THE INVENTION

The cultivar 'AMIECH1602' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1602'. These characteristics in combination distinguish 'AMIECH1602' as a new and distinct *Echeveria pulidonis* cultivar:

1. 'AMIECH1602' exhibits thick, succulent foliage with an upwardly curved attitude and tightly arranged in a compact rosette; and
2. 'AMIECH1602' exhibits broad obovate to broad oblanceolate foliage with an obtusely cuspidate apex; and
3. 'AMIECH1602' exhibits moderately pruinose foliage; and
4. 'AMIECH1602' exhibits foliage with a blue-grey general coloration with pink margins.

BOTANICAL DESCRIPTION OF THE PLANT

Figure 1:
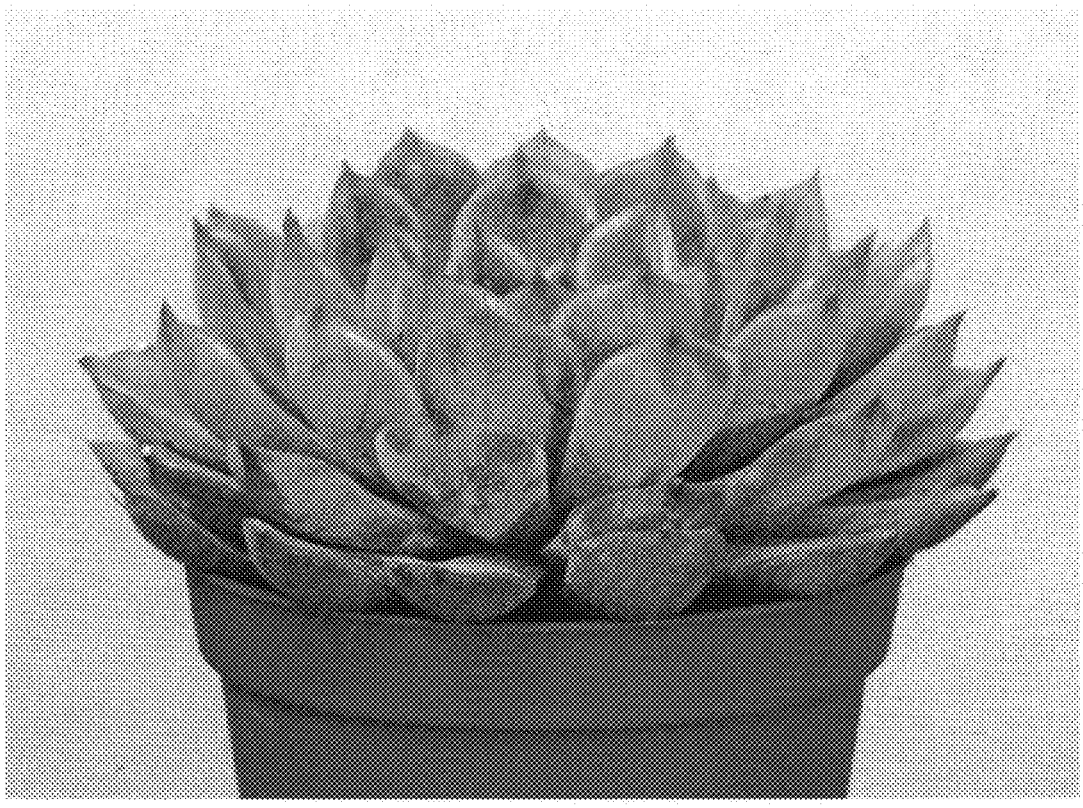
FIG. 1 illustrates, as nearly true as it is reasonably possible to make the same in color photographs of this type, an exemplary plant of 'AMIECH1602' grown in a commercial greenhouse in Heerhugowaard, the Netherlands. This plant is approximately 9 months old, shown planted in an 8.5 cm container.
Figure 2:
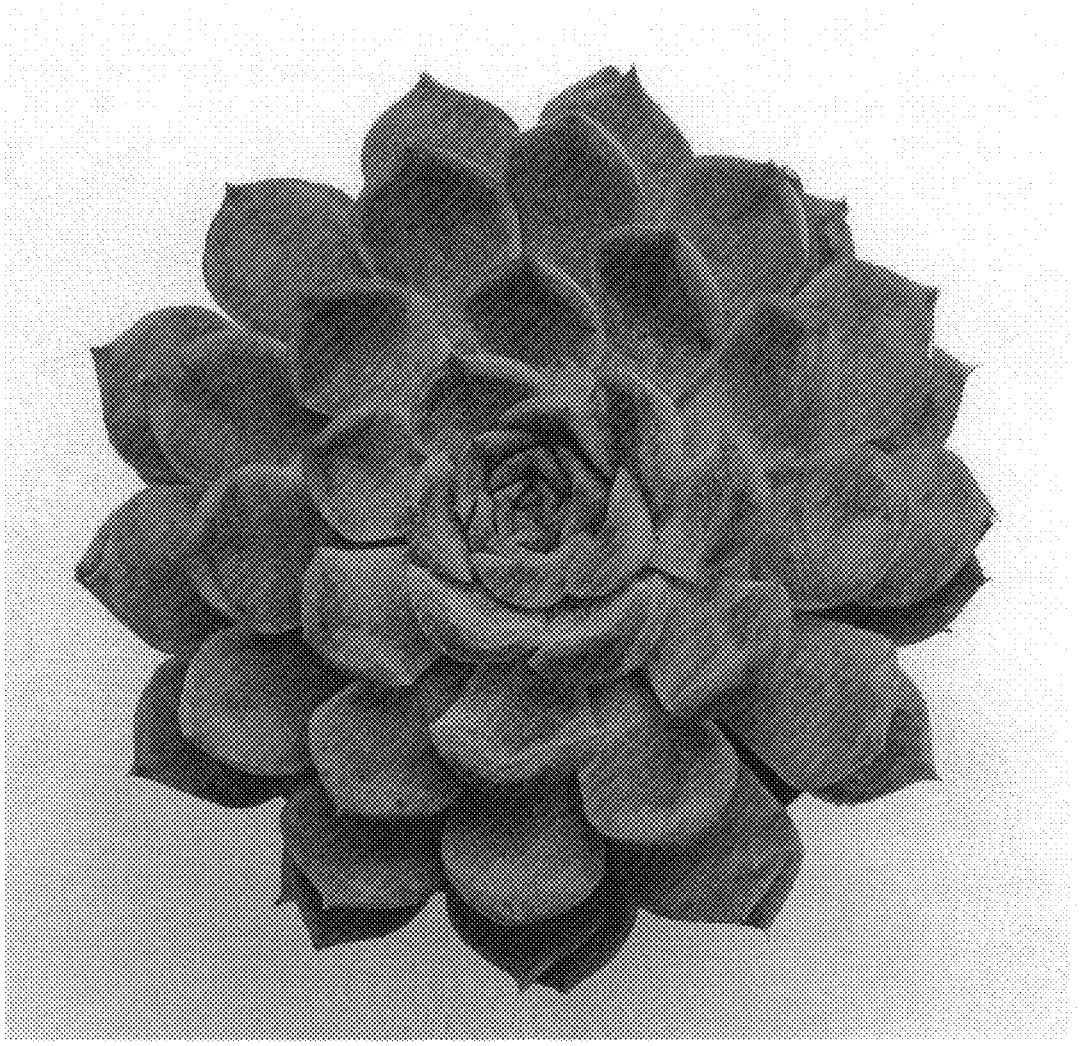
FIG. 2 illustrates, as nearly true as it is reasonably possible to make the same in color photographs of this type, the typical foliage arrangement of 'AMIECH1602.
Figure 3:
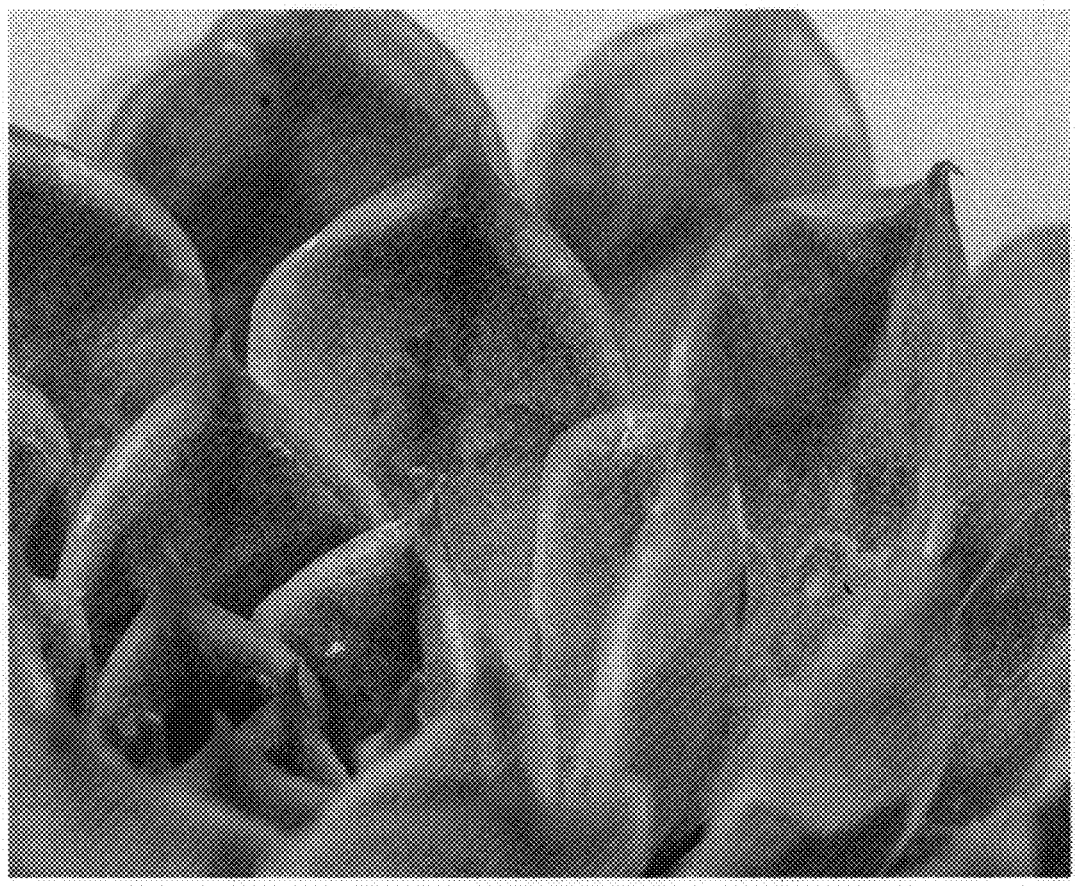
FIG. 3 illustrates, as nearly true as it is reasonably possible to make the same in color photographs of this type, the foliage color from the center of the rosette (juvenile foliage) to the outer most whorl of the rosette (mature foliage) of 'AMIECH1602'.
Figure 4:
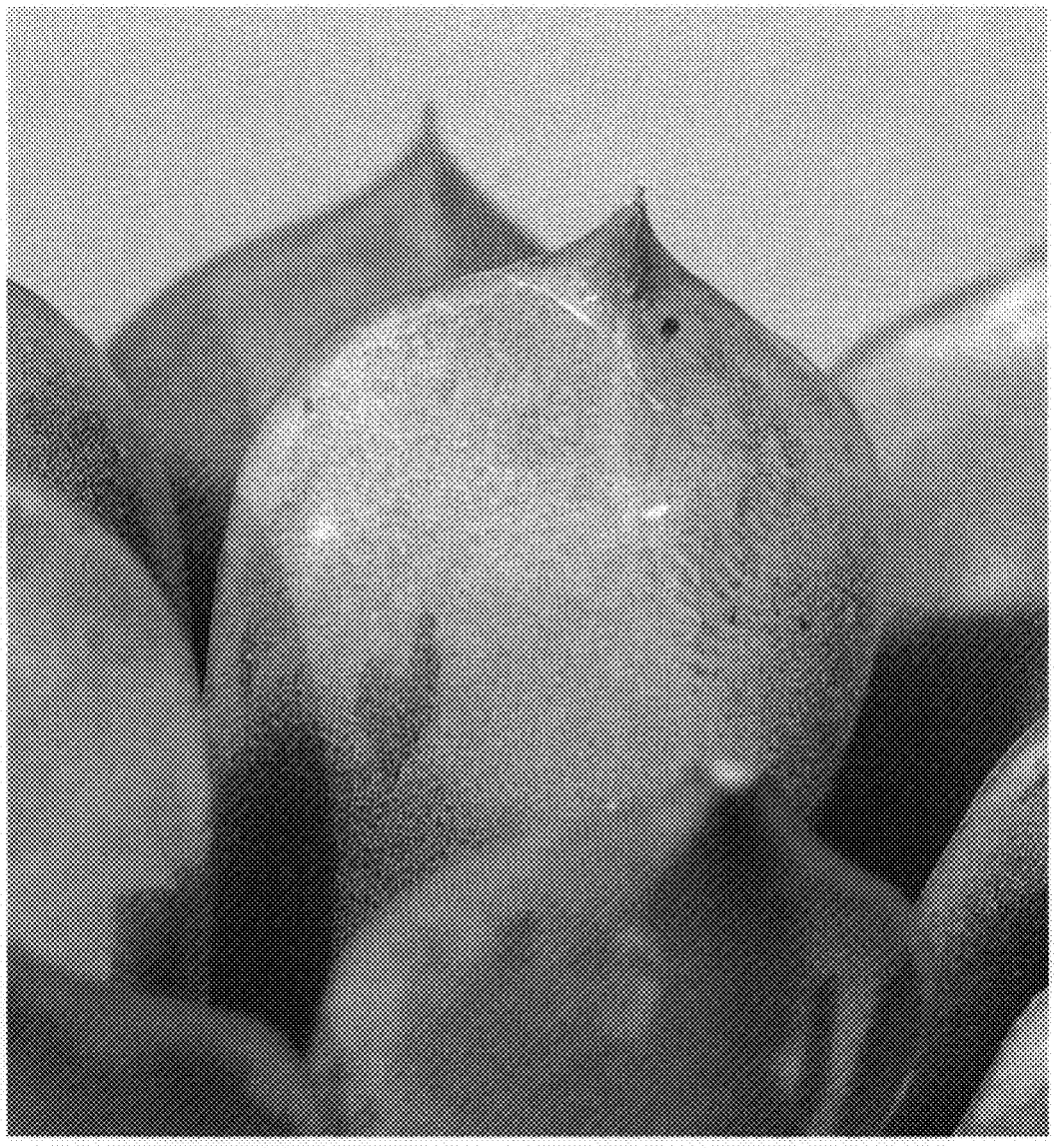
FIG. 4 illustrates, as nearly true as it is reasonably possible to make the same in color photographs of this type, the abaxial surface of the mature foliage 'AMIECH1602'.

The following observations and measurements made in November of 2016 describe averages from a sample set of six specimens of 9 months old 'AMIECH1602' plants grown in 8.5 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1602' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1602' and a comparison with the parent and closest known comparator, *Echeveria pulidonis*, is provided below.

Plant description:

*Growth habit*.—Succulent perennial with foliage growing in a non-branched basal rosette.

*Plant shape*.—Flattened globular.

*Height from soil level to top of foliar plane*.—5.5 cm.

*Plant spread*.—Average of 11.3 cm.

*Growth rate*.—Low.

*Plant vigor*.—Low.

*Propagation*.—Type — Leaf cuttings. Time to initiate rooting — Approximately 21 to 35 days at 18 degrees Celsius. Crop time — Approximately 18 to 22 weeks to produce a marketable plant in an 11 cm container.

*Disease and pest resistance or susceptibility*.—Neither resistance nor susceptibility to typical *Echeveria agavoides* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 62 leaves per rosette.

*Shape*.—Thick, succulent leaves which are obovate to broad oblanceolate.

*Dimensions*.—5.3 cm long, 2.0 cm wide, and 0.7 cm thick, on average.

*Aspect*.—Slightly concave and carinate.

*Attitude*.—Slightly to moderately curved upward.

*Apex*.—Obtusely cuspidate, with point curling downward.

*Base*.—Cuneate.

*Margin*.—Entire; not undulated or lobed.

*Pubescence, texture and luster of the adaxial surface*.—Glabrous, smooth, and matte; heavily pruinose, colored greyed-green, in between RHS 188B and 188C.

*Pubescence, texture and luster of the abaxial surface*.—Glabrous, smooth, and matte; heavily pruinose, colored greyed-green, in between RHS 188B and 188C.

*Color*.—Juvenile foliage, adaxial surface — Greyed-green, nearest to RHS 191A, and fading lighter towards the base, nearest to RHS 193A; margins are considerably lighter, in between RHS 192C and 192D; apex and margins nearest to the apex are greyed-purple, in between RHS 185B and 185C. Juvenile foliage, abaxial surface — Greyed-green, in between RHS 191A and 191B, and fading lighter towards the base, in between RHS 193B and 193C; margins are considerably lighter, in between RHS 192C and 192D; apex and margins near the apex are greyed-purple, nearest to RHS 185B. Mature foliage, adaxial surface — Yellow-green, nearest to RHS 148B, and fading lighter towards the base, nearest to RHS 147D; base is red-purple, nearest to RHS 63C; margins are greyed-green, in between RHS 192C and 192D; apex and margins nearest to the apex are greyed-red, in between RHS 182A and 182B. Mature foliage, abaxial surface — Yellow-green, in between RHS 148B to 148C, and fading lighter towards the base, nearest to RHS 147D; base is red-purple, nearest to RHS 63C; margins are greyed-green, in between RHS 193A and 193B; apex and margins nearest to the apex are greyed-red, in between RHS 182A and 182B.

*Venation*.—No venation is visible.

*Petiole*.—No petiole; leaves are sessile.

Inflorescence: No flowering has been observed to date.

Comparisons with the parent plant and closest known comparator: Plants of the new cultivar 'AMIECH1602' differ from the parent, *Echeveria pulidonis*, which is also the closest known comparator, in the following characteristics described in Table 1 below.

TABLE 1

| Characteristic | 'AMIECH1602' | *Echeveria pulidonis* |
|---|---|---|
| Leaf thickness. | Thicker than the parent. | Thinner than 'AMIECH1602'. |
| Leaf apex. | Obtusely cuspidate. | Acutely cuspidate. |
| Leaf width. | Wider than the parent. | Narrower than 'AMIECH1602'. |
| General coloration of mature foliage. | Heavily pruinose, giving the foliage a greyed-green to blue-grey appearance. | Moderately pruinose, giving the foliage a greyed-green appearance. |
| Mature foliage; general coloration of the margins. | Pink. | Dark red-purple. |

Plants of the new cultivar 'AMIECH1606' differ from the commercial variety, *Echeveria agavoides* 'Hercules ' (U.S. Plant Pat. No. 26,230), in the following characteristics described in Table 2 below.

TABLE 2

| Characteristic | 'AMIECH1606' | 'Hercules' |
|---|---|---|
| Plant size | Larger than 'Hercules'. | Smaller than 'AMIECH1602'. |
| General coloration of mature foliage. | Heavily pruinose, giving the foliage a greyed-green to blue-grey appearance. | Moderately pruinose, giving the foliage a greyed-green appearance. |
| Mature foliage; general coloration of the apex and margins | In between RHS 182A and 182B; appearing as pink. | RHS 183C; appearing as greyed-red. |

That which is claimed is:

1. A new and distinct variety of *Echeveria pulidonis* plant named 'AMIECH1602', substantially as described and illustrated herein.

* * * * *